(12) United States Patent
Molin et al.

(10) Patent No.: US 7,807,440 B2
(45) Date of Patent: Oct. 5, 2010

(54) **PROBIOTIC *LACTOBACILLUS* STRAINS FOR IMPROVED VAGINAL HEALTH**

(75) Inventors: Göran Molin, Lund (SE); Siv Ahrné, Lund (SE); Bengt Jeppsson, Lund (SE); Alejandra Vasquez, Malmö (SE); Anna Berggren, Flyinge (SE)

(73) Assignee: Probi AB, Lund (SE)

( * ) Notice: Subject to any disclaimer, the term of this patent is extended or adjusted under 35 U.S.C. 154(b) by 490 days.

(21) Appl. No.: 11/662,288

(22) PCT Filed: Oct. 5, 2005

(86) PCT No.: PCT/SE2005/001467

§ 371 (c)(1),
(2), (4) Date: Apr. 11, 2007

(87) PCT Pub. No.: WO2006/038869

PCT Pub. Date: Apr. 13, 2006

(65) Prior Publication Data

US 2008/0268006 A1 Oct. 30, 2008

(30) Foreign Application Priority Data

Oct. 5, 2004 (SE) .................................... 0402406

(51) Int. Cl.
*C12N 1/12* (2006.01)

(52) U.S. Cl. .................................................. 435/252.1

(58) Field of Classification Search ........................ None
See application file for complete search history.

(56) References Cited

U.S. PATENT DOCUMENTS

| | | | |
|---|---|---|---|
| 5,895,758 A | 4/1999 | Majnarich et al. | |
| 6,159,465 A | 12/2000 | Adlerberth et al. | |
| 6,180,100 B1 | 1/2001 | Bruce et al. | |
| 6,830,750 B1 | 12/2004 | Naruszewicz | |
| 2002/0090365 A1 | 7/2002 | Chrisope | |
| 2002/0094328 A1 * | 7/2002 | De Simone | 424/93.45 |

FOREIGN PATENT DOCUMENTS

WO WO 03/080813 A2 10/2003
WO WO 2004/087893 A1 10/2004

OTHER PUBLICATIONS

Famularo G. et al., *Microecology, bacterial vaginosis and probiotics: perspectives for bacteriotherapy*, Medical *Hypotheses* (2001) 56(4), 421-430.
Reid, Gregor et al., *Oral probiotics can resolve urogenital infections*, FEMS Immunology and Medical Microbiology 30 (2001) 49-52.
Reid, G. et al., *Urogenital infections in women: can probiotics help?*, Postgrad Med J 2003; 79:428-432.
Vásquez, Alejandra et al., *Vaginal Lactobacillus Flora of Healthy Swedish Women*, Journal of Clinical Microbiology, American Society of Microbiology, Aug. 2002, vol. 40, No. 8, p. 2746-2749.
Mark Wilks et al., Journal of Clinical Microbiology, Feb. 2004, vol. 42, No. 2, pp. 713-717 entitled "Identification and $H_2O_2$ Production of Vaginal Lactobacilli from Pregnant Women at High Risk of Preterm Birth and Relation with Outcome".
Ana C. Vallor et al., The Journal of Infectious Diseases, Dec. 1, 2001, vol. 184, pp. 1431-1436, entitled "Factors Associated with Acquisition of, or Persistant Colonization by, Vaginal Lactobacilli: Role of Hydrogen Peroxide Production".
Jordi Osset et al., The Journal of Infectious Diseases, 2001, vol. 183, pp. 485-491, entitled "Assessment of the Capacity of *Lactobacillus* to Inhibit the Growth of Uropathogens and Block Their Adhesion to Vaginal Epithelial Cells".
P. Mastromarino et al., Journal of Applied Microbiology 2002, vol. 93, pp. 884-893, entitled "Characterization and Selection of Vaginal *Lactobacillus* Strains for the Preparation of Vaginal Tablets".
Susanna Cunningham-Rundles et al., The American Journal of Gastroenterology 2000, vol. 95, No. 1, Supplement pp. 22-25, entitled "Probiotics and Immune Response".

* cited by examiner

*Primary Examiner*—Mark Navarro
(74) *Attorney, Agent, or Firm*—Buchanan Ingersoll & Rooney PC

(57) ABSTRACT

The present invention relates to a probiotic bacterial strain belonging to the genus *Lactobacillus* having the ability to colonize the human vagina, or a variant thereof. More specifically the probiotic bacterial strain belongs to a species chosen from the group comprising *Lactobacillus plantarum*, *Lactobacillus crispatus*, and *Lactobacillus gasseri*. Further it relates to its use as a medicament, a composition comprising the strain, the composition, e.g., being a food product or a pharmaceutical composition, a hygiene product, a biological pure culture of the strain, and a novel food.

27 Claims, 15 Drawing Sheets

SEQUENCE LISTING

```
<160> NUMBER OF SEQ ID NOS: 1

<210> SEQ ID NO 1
<211> LENGTH: 10
<212> TYPE: DNA
<213> ORGANISM: Lactobacillus plantarum

<400> SEQUENCE: 1
ccgcagccaa                                                         10
```

US 7,807,440 B2

PROBIOTIC *LACTOBACILLUS* STRAINS FOR IMPROVED VAGINAL HEALTH

FIELD OF THE INVENTION

The present invention relates to a probiotic bacterial strain belonging to the genus *Lactobacillus*, or a variant thereof, having the ability to colonize the human vagina. More specifically the probiotic bacterial strain belongs to a species chosen from the group comprising *Lactobacillus plantarum*, *Lactobacillus crispatus* and *Lactobacillus gasseri*. Further it relates to its use as a medicament, a composition comprising said strain, the composition e g being a food product or a pharmaceutical composition, a hygiene product, a biological pure culture of said strain and a novel food.

BACKGROUND OF THE INVENTION

The healthy vagina is maintained by the interaction of the vaginal epithelium and the microbial flora, where lactobacilli play a crucial role. *Lactobacillus* species maintain the pH acidity in the vagina by the glucose metabolism; moreover, together with the hydrogen peroxide and bacteriocin-like production they suppress the growth of pathogens and other unwanted microorganisms. This contributes to a successful protection against uropathogens causing urinary tract infection (UTI), the disorder bacterial vaginosis and yeast vaginitis by *Candida albicans* (Reid G, Bruce A W. Urogenital infections in women: can probiotics help? Postgrad Med J 2003; 79: 428-432.).

The *Lactobacillus* species dominating in the vagina has for long been accepted to be *Lactobacillus acidophilus*, but the use of genotypic identification methods have demonstrated that the most common lactobacilli species in the healthy vagina are actually *Lactobacillus crispatus*, *Lactobacillus gasseri*, *Lactobacillus iners* and *Lactobacillus jensenii*. However, separate studies demonstrate differences between the lactobacilli recovered from the vagina showing species such as *Lactobacillus rhamnosus*, *Lactobacillus pentosus*, *Lactobacillus fermentum*, *Lactobacillus plantarum* and *Lactobacillus acidophilus* as the dominating lactobacilli, this is probably due to differences in the handling of samples, vaginal status or the methods preferred for the isolation (Vasquez A, Jakobsson T, Ahrné S, Forsum U, Molin G. Vaginal *Lactobacillus* flora of healthy Swedish women. J. Clin. Mirobiol. 2002; 40: 2746-9).

The World Health Organization defined probiotics as "live microorganisms which when administered in adequate amounts confer a health benefit on the host". The development of antibiotic resistance and failures in vaginal infections treatment have risen an increased interest in probiotics as an alternative tool. The need for a vaginal probiotic is clear in terms of the high number of incidence of vaginal infections recurrence (Reid G, Bruce A W, Fraser N, Heinemann C, Owen J, Henning B. Oral probiotics can resolve urogenital infections. FEMS Immunol Med Microbiol 2001; 30: 49-52; Famularo G, Pieluigi M, Coccia R, Mastroiacovo P, De Simone C. Microecology, bacterial vaginosis and probiotics: perspectives for bacteriotherapy. Med Hypotheses 2001; 56: 421-30.). A change in the vaginal flora characterized by the decrease of lactobacilli appears to be the major factor causing the syndrome bacterial vaginosis. Regular administration of a *Lactobacillus* strain with ability to colonize vagina can be an alternative solution for this problem.

Yoghurt treatment as a household remedy has been used for years for prevention or relief of vaginal disorders. However, *Lactobacillus delbreukii* var. *bulgaricus*, the lactobacilli found in yogurt is not an optimal candidate for vaginal restoration by probiotics because it's not normally found in that environment and does not adhere well to the vaginal epithelial cells for successful colonization (Famularo G, Pieluigi M, Coccia R, Mastroiacovo P, De Simone C. Microecology, bacterial vaginosis and probiotics: perspectives for bacteriotherapy. Med Hypotheses 2001; 56: 421-430). The optimal candidates for such a vaginal probiotic are species that are normally found in the vagina and possess qualities to suppress pathogens.

The normal vaginal flora ascends from the rectal mucosa (Reid G, Bruce A W. Urogenital infections in women: can probiotics help? Postgrad Med J 2003; 79: 428-432), which means that orally administrated microorganisms that survive the gastrointestinal passage will appear in the vagina after a certain time. This fact raises the possibility of a vaginal probiotic that can be given orally to the host which simplify long term administration with the intention to prevent vaginal problems.

Women given *L. acidophilus* during 6 moths resulting in a decrease in both candidal colonization and infection (Hilton E, Isenberg H D, Alperstein P, France K, Borenstein M T. Ingestion of yogurt containing *Lactobacillus acidophilus* as prophylaxis for candidal vaginitis. Ann Internal Med 1992; 116: 353-357).

SUMMARY OF THE INVENTION

It has now surprisingly been found that specific probiotic bacterial strains belonging to the genus *Lactobacillus*, and more specifically to a species chosen from the group comprising *Lactobacillus plantarum*, *Lactobacillus crispatus* and *Lactobacillus gasseri*, have the ability to colonize the human vagina and preserve or improve the vaginal health when administered e g orally, rectally or vaginally.

In one aspect the present invention relates to a probiotic bacterial strain belonging to the genus *Lactobacillus*, or a variant thereof, having the ability to colonize the human vagina with the proviso that the bacterial strain is not *Lactobacillus plantarum* HEAL 9, which was deposited, under the provisions of the Budapest Treaty, at Deutsche Sammlung von Mikroorganismen und Zellkulturen GmbH, Mascheroder Weg 1b, D-38124, Braunschweig, Germany on Nov. 27, 2002 and has been assigned accession number DSM 15312, *Lactobacillus plantarum* HEAL 19, which was deposited, under the provisions of the Budapest Treaty, at Deutsche Sammlung von Mikroorganismen und Zellkulturen GmbH, Mascheroder Weg 1b, D-38124, Braunschweig, Germany on Nov. 27, 2002 and has been assigned accession number DSM 15313, *Lactobacillus plantarum* HEAL 99, which was deposited, under the provisions of the Budapest Treaty, at Deutsche Sammlung von Mikroorganismen und Zellkulturen GmbH, Mascheroder Weg 1b, D-38124, Braunschweig, Germany on Nov. 27, 2002 and has been assigned accession number DSM 15316, Lactobacillus plantarum 299, which was deposited, under the provisions of the Budapest Treaty, at DSM-Deutsche Sammlung von Mikroorganismen und Zellkulturen GmbH, Mascheroder Weg 1b, D-38124, Braunschweig, Germany on Jul. 2, 1991 and has been assigned accession number DSM 6595, or *Lactobacillus plantarum* 299v, which was deposited, under the provisions of the Budapest Treaty, at DSM-Deutsche Sammlung von Mikroorganismen und Zellkulturen GmbH, Mascheroder Weg 1b, D-38124, Braunschweig, Germany on Mar. 16, 1995 and has been assigned accession number as DSM 9843.

In one embodiment said bacterial strain belongs to a species chosen from the group comprising *Lactobacillus plan-*

*tarum, Lactobacillus crispatus* and *Lactobacillus gasseri*, or a variant thereof, and in another embodiment said strain has a mannose-specific adhesin or other adhesive mechanisms that allow the bacteria to bind to the inner surface of the vagina, the gastro intestinal tract, urinary bladder including the urethra.

In one embodiment of the invention the probiotic bacterial strain is *Lactobacillus crispatus* VPC5, which was deposited, under the provisions of the Budapest Treaty, at Deutsche Sammlung von Mikroorganismen und Zellkulturen GmbH, Mascheroder Weg 1b, D-38124, Braunschweig, Germany on Sep. 17, 2004 and has been assigned accession number DSM 16735, or a variant thereof.

In another embodiment of the invention the probiotic bacterial strain is *Lactobacillus crispatus* VPC40, which was deposited, under the provisions of the Budapest Treaty, at Deutsche Sammlung von Mikroorganismen und Zellkulturen GmbH, Mascheroder Weg 1b, D-38124, Braunschweig, Germany on Sep. 17, 2004 and has been assigned accession number DSM 16736, or a variant thereof.

In still another embodiment of the invention the probiotic bacterial strain is *Lactobacillus crispatus* VPC70, which was deposited, under the provisions of the Budapest Treaty, at Deutsche Sammlung von Mikroorganismen und Zellkulturen GmbH, Mascheroder Weg 1b, D-38124, Braunschweig, Germany on Sep. 17, 2004 and has been assigned accession number DSM 16738, or a variant thereof.

In a yet further embodiment the probiotic bacterial strain is *Lactobacillus crispatus* VPC71, which was deposited, under the provisions of the Budapest Treaty, at Deutsche Sammlung von Mikroorganismen und Zellkulturen GmbH, Mascheroder Weg 1b, D-38124, Braunschweig, Germany on Sep. 17, 2004 and has been assigned accession number DSM 16739, or a variant thereof.

In a yet further embodiment the probiotic bacterial strain is *Lactobacillus crispatus* VPC77, which was deposited, under the provisions of the Budapest Treaty, at Deutsche Sammlung von Mikroorganismen und Zellkulturen GmbH, Mascheroder Weg 1b, D-38124, Braunschweig, Germany on Sep. 17, 2004 and has been assigned accession number DSM 16740, or a variant thereof.

In another embodiment the probiotic bacterial strain is *Lactobacillus crispatus* VPC111, which was deposited, under the provisions of the Budapest Treaty, at Deutsche Sammlung von Mikroorganismen und Zellkulturen GmbH, Mascheroder Weg 1b, D-38124, Braunschweig, Germany on Sep. 17, 2004 and has been assigned accession number DSM 16741, or a variant thereof.

In yet another embodiment the probiotic bacterial strain is *Lactobacillus crispatus* VPC 130, which was deposited, under the provisions of the Budapest Treaty, at Deutsche Sammlung von Mikroorganismen und Zellkulturen GmbH, Mascheroder Weg 1b, D-38124, Braunschweig, Germany on Sep. 17, 2004 and has been assigned accession number DSM 16742, or a variant thereof.

In yet another embodiment the probiotic bacterial strain is *Lactobacillus crispatus* VPC 177, which was deposited, under the provisions of the Budapest Treaty, at Deutsche Sammlung von Mikroorganismen und Zellkulturen GmbH, Mascheroder Weg 1b, D-38124, Braunschweig, Germany on Sep. 17, 2004 and has been assigned accession number DSM 16743, or a variant thereof.

In a further embodiment the probiotic bacterial strain is *Lactobacillus gasseri* VPG44, which was deposited, under the provisions of the Budapest Treaty, at Deutsche Sammlung von Mikroorganismen und Zellkulturen GmbH, Mascheroder Weg 1b, D-38124, Braunschweig, Germany on Sep. 17, 2004 and has been assigned accession number DSM 16737, or a variant thereof.

In yet another embodiment the bacterial strains described above are used as a medicament.

In a second aspect the present invention relates to the use of a bacterial strain as described above for the manufacturing of a medicament for treatment and/or prophylaxis of bacterial vaginosis, viral vaginosis, yeast vaginitis, infections in the vagina, sexually transmitted diseases, such as HIV and chlamydia infection, infections endangering the foetus in pregnant women, preterm labour and urinary tract infection.

In a third aspect the present invention relates to the use of a bacterial strain chosen from the group comprising *Lactobacillus plantarum* HEAL 9, deposition number DSM 15312, *Lactobacillus plantarum* HEAL 19, deposition number DSM 15313, *Lactobacillus plantarum* HEAL 99, deposition number DSM 15316, *Lactobacillus plantarum* 299, deposition number DSM 6595, or *Lactobacillus plantarum* 299v, deposition number DSM 9843, or a variant thereof, for the manufacturing of a medicament for treatment and/or prophylaxis of bacterial vaginosis, viral vaginosis, yeast vaginitis, infections in the vagina, sexually transmitted diseases, such as HIV and chlamydia infection, infections endangering the foetus in pregnant women, preterm labour and urinary tract infection with the proviso *Lactobacillus plantarum* 299v, deposition number DSM 9843 for urinary tract infection.

In a fourth aspect the present invention relates to a composition comprising at least one probiotic bacterial strain as described above, and/or *Lactobacillus plantarum* HEAL 9, deposition number DSM 15312, *Lactobacillus plantarum* HEAL 19, deposition number DSM 15313, *Lactobacillus plantarum* HEAL 99, deposition number DSM 15316, *Lactobacillus plantarum* 299, deposition number DSM 6595, or *Lactobacillus plantarum* 299v, deposition number DSM 9843, or a variant thereof, and/or a fragment or fraction thereof. In one embodiment the composition comprises a carrier material.

In another embodiment the composition is a food product, preferably comprising a carrier material chosen from the group comprising oat meal gruel, lactic acid fermented foods, resistant starch, dietary fibers, carbohydrates, proteins and glycosylated proteins. In still another embodiment said food product is chosen from the group comprising bread, cheese, yogurt, juice, health bars, spreads, biscuits and cereals, and in yet another one said at least one probiotic bacterial strain is encapsulated or coated, and preferably present in an amount giving, when consumed, an effective daily dose of $10^7$ to $10^{12}$ CFU, preferably from $10^9$ to $10^{10}$ CFU.

In a further embodiment the composition is a food supplement, preferably comprising a carrier material chosen from the group comprising oat meal gruel, lactic acid fermented foods, resistant starch, dietary fibers, inulines, carbohydrates, proteins and glycosylated proteins.

In still another embodiment the composition is a pharmaceutical composition for treatment and/or prophylaxis of bacterial vaginosis, viral vaginosis, yeast vaginitis, infections in the vagina, sexually transmitted diseases, such as HIV and chlamydia infection, infections endangering the foetus in pregnant women, preterm labour and urinary tract infection, with the proviso *Lactobacillus plantarum* 299v, deposition number DSM 9843 for urinary tract infection.

In one embodiment said pharmaceutical composition is administered orally, vaginally or rectally, or instilled into the urinary bladder, and preferably said carrier material is at least one pharmaceutically acceptable carrier.

In a further embodiment said pharmaceutical composition is administered in a combined administration treatment of orally and vaginally, orally and rectally, or orally, vaginally and rectally.

In another embodiment said pharmaceutical composition is administered in the form of tablets, sucking tablets, sweets, chewing gum, capsules, enterocoated tablets and capsules, suppositories, micro-enemas, vaginal tablets, vaginal gelatin capsules, vaginal troches, cream, gel, ointment, lotion, tampons, napkins, pads, melting strips, condoms, pessaries, sprays and clinical nutrition product. In still another embodiment of the composition, when administered orally, said at least one probiotic bacterial strain is present in an amount giving an effective daily dose of from $10^7$ to $10^{12}$ CFU, preferably from $10^9$ to $10^{10}$ CFU, and when administered vaginally or rectally, said at least one probiotic bacterial strain is present in an amount giving an effective daily dose of from $10^3$ to $10^{12}$ CFU, preferably from $10^5$ to $10^9$ CFU.

In one embodiment of the pharmaceutical composition said at least one probiotic bacterial strain is encapsulated or coated, and in another embodiment the composition comprises additives chosen from the group comprising vitamins, minerals, and prebiotics.

In a fifth aspect the present invention relates to a hygiene product comprising a composition as described above. In one embodiment said hygiene product is chosen from the group comprising tampons, sanitary napkins, sanitary pads, diapers, soaps, shampoos, gels, ointments, creams, sprays and lotions.

In a sixth aspect the present invention relates to a biological culture of at least one probiotic bacterial strain as described above, and/or *Lactobacillus plantarum* HEAL 9, deposition number DSM 15312, *Lactobacillus plantarum* HEAL 19, deposition number DSM 15313, *Lactobacillus plantarum* HEAL 99, deposition number DSM 15316, *Lactobacillus plantarum* 299, deposition number DSM 6595, *Lactobacillus plantarum* 299v, deposition number DSM 9843, or a variant thereof, and/or a fragment or fraction thereof.

In a seventh aspect the present invention relates to a novel food comprising at least one probiotic bacterial strain as described above, and/or *Lactobacillus plantarum* HEAL 9, deposition number DSM 15312, *Lactobacillus plantarum* HEAL 19, deposition number DSM 15313, *Lactobacillus plantarum* HEAL 99, deposition number DSM 15316, *Lactobacillus plantarum* 299, deposition number DSM 6595, *Lactobacillus plantarum* 299v, deposition number DSM 9843, or a variant thereof, and/or a fragment or fraction thereof.

In an eighth aspect the present invention relates to a food supplement comprising at least one probiotic bacterial strain as described above and/or *Lactobacillus plantarum* HEAL 9, deposition number DSM 15312, *Lactobacillus plantarum* HEAL 19, deposition number DSM 15313, *Lactobacillus plantarum* HEAL 99, deposition number DSM 15316, *Lactobacillus plantarum* 299, deposition number DSM 6595, *Lactobacillus plantarum* 299v, deposition number DSM 9843, or a variant thereof, and/or a fragment or fraction thereof.

In one embodiment said probiotic bacterial strain is viable. In another embodiment it is inactivated or suppressed. In still another embodiment it is genetically modified, and in still another one it is killed.

In an eighth aspect of the present invention relates to a fragment or fraction of a probiotic bacterial strain as described above.

DESCRIPTION OF THE INVENTION

Figure 1:
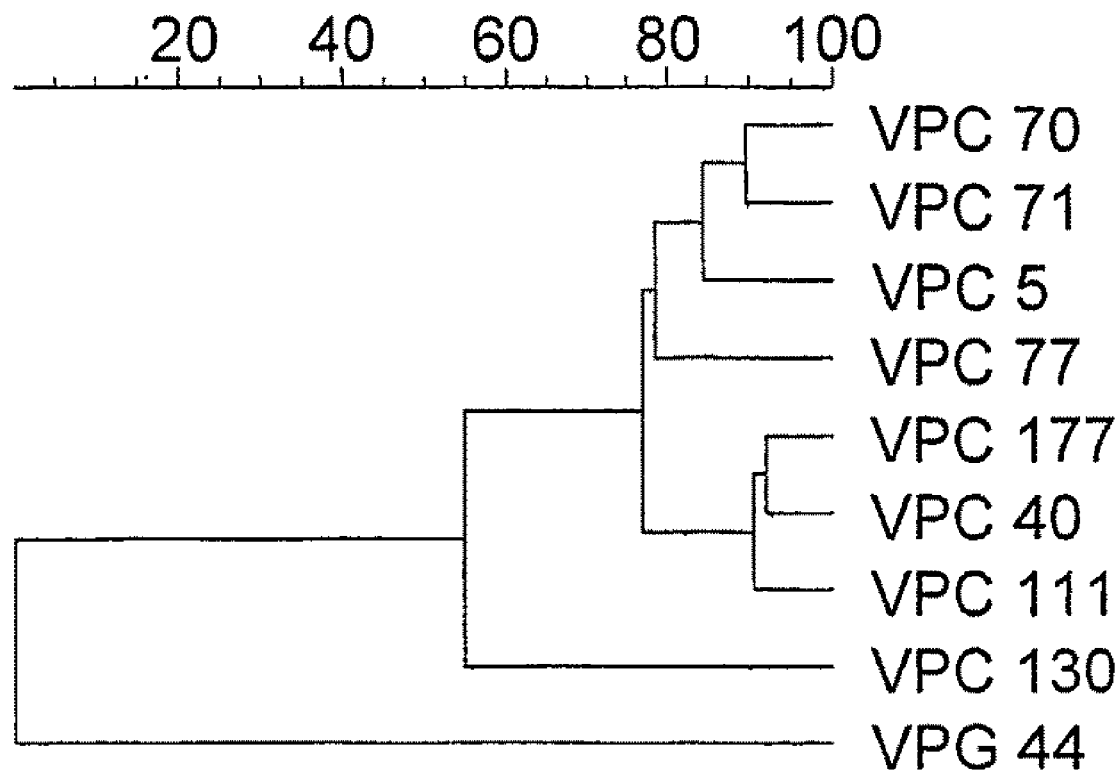
FIG. 1 shows a dendrogram based on the RAPD-analyses of some of the most preferred probiotic bacterial strains.
Figure 2A:
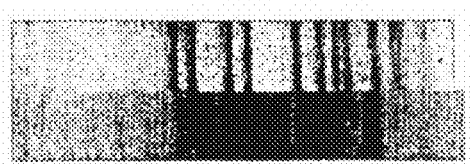
FIG. 2 A-I shows the RAPD patterns for some of the most preferred probiotic bacterial strains on which the dendrogram of FIG. 1 is based.
Figure 2B:
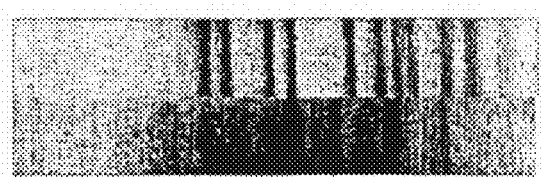
Figure 2C:
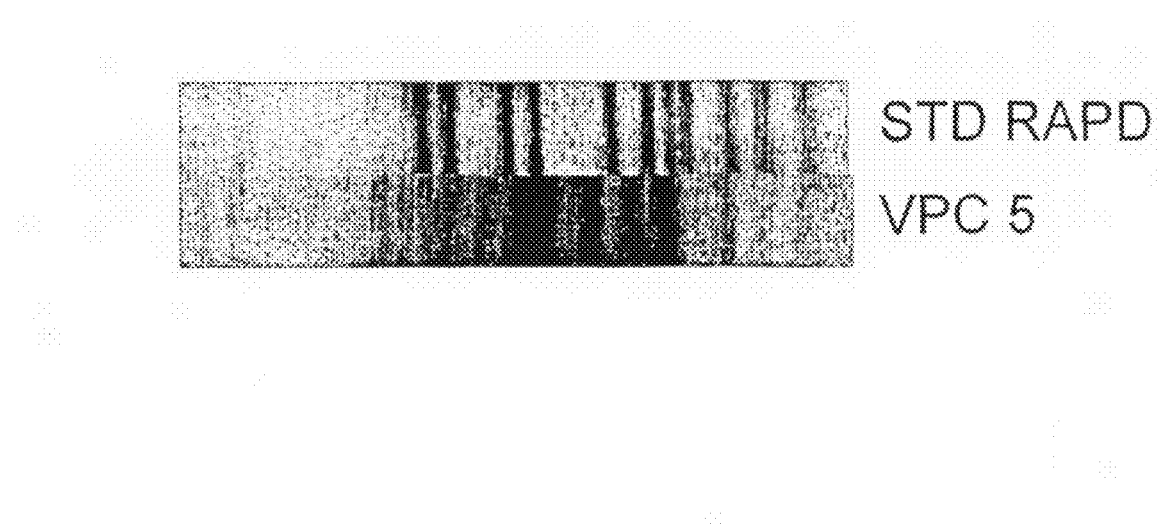
Figure 2D:
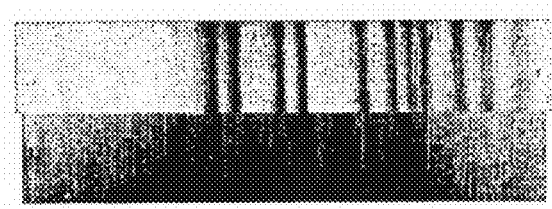
Figure 2E:
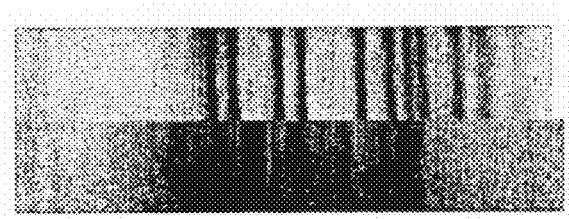
Figure 2F:
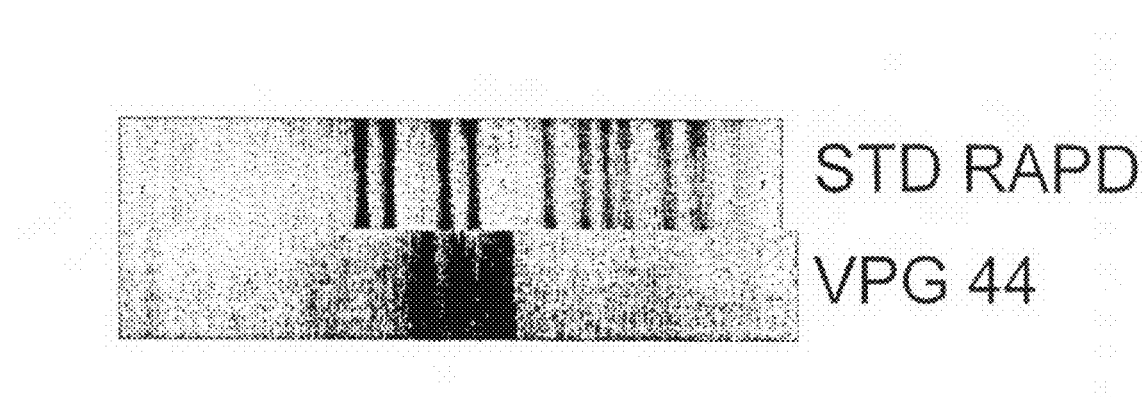
Figure 2G:
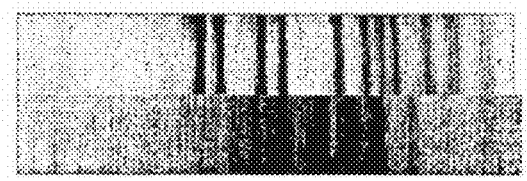
Figure 2H:
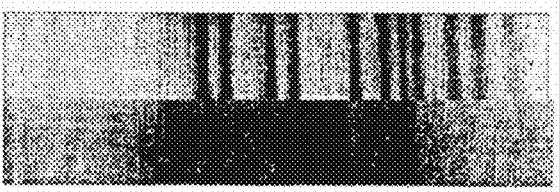
Figure 2I:
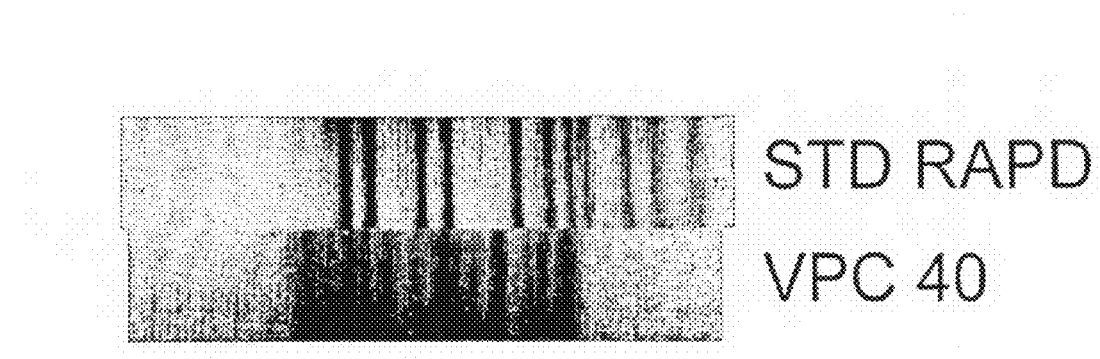
Figure 3A:
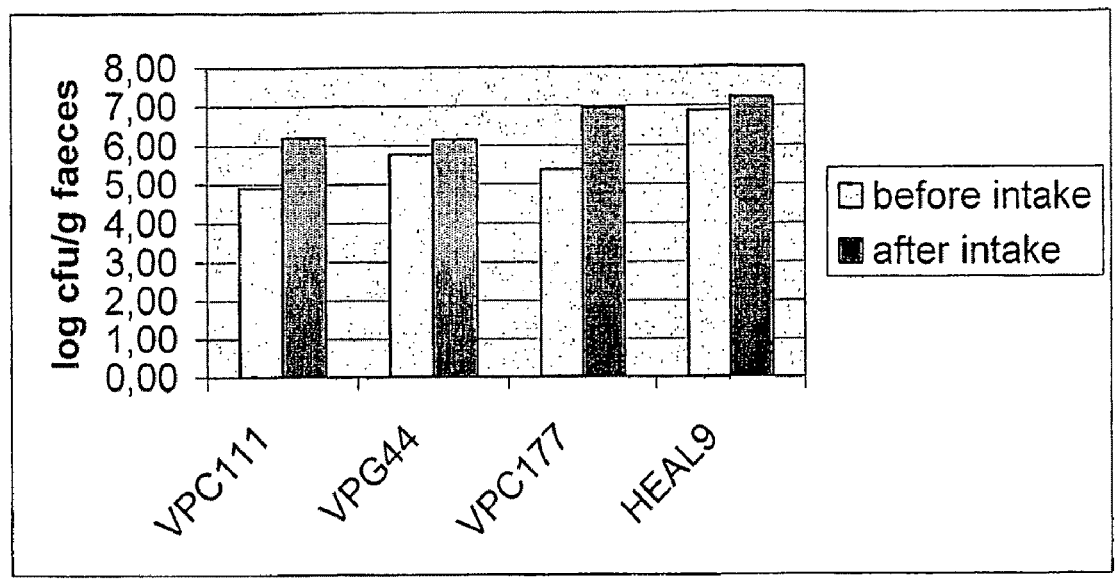
FIG. 3A shows log cfu/g faeces after intake of the four different experimental products of example 3.
Figure 3B:
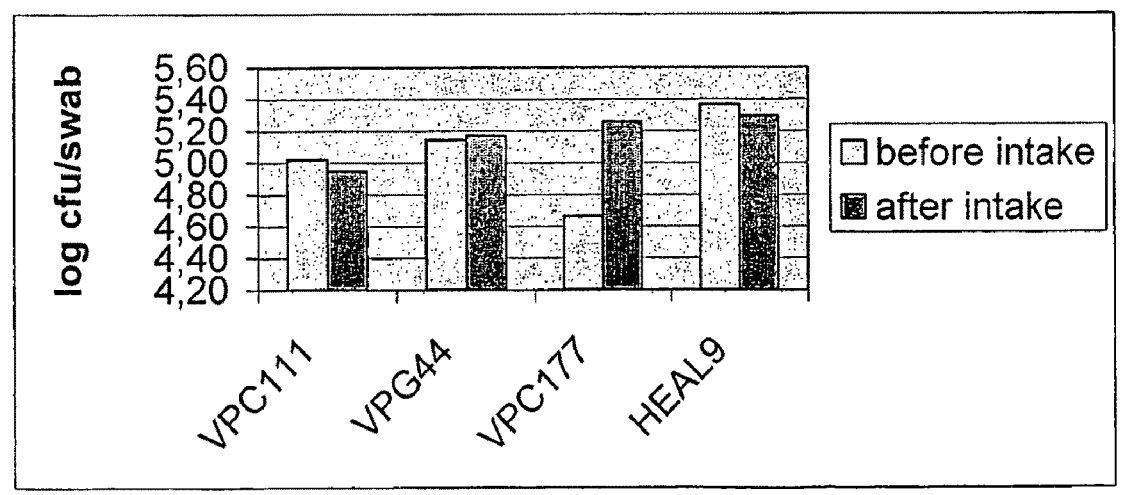
FIG. 3B shows log cfu/swab in vaginal fluid after intake of the four different experimental products of example 3.
Figure 4:
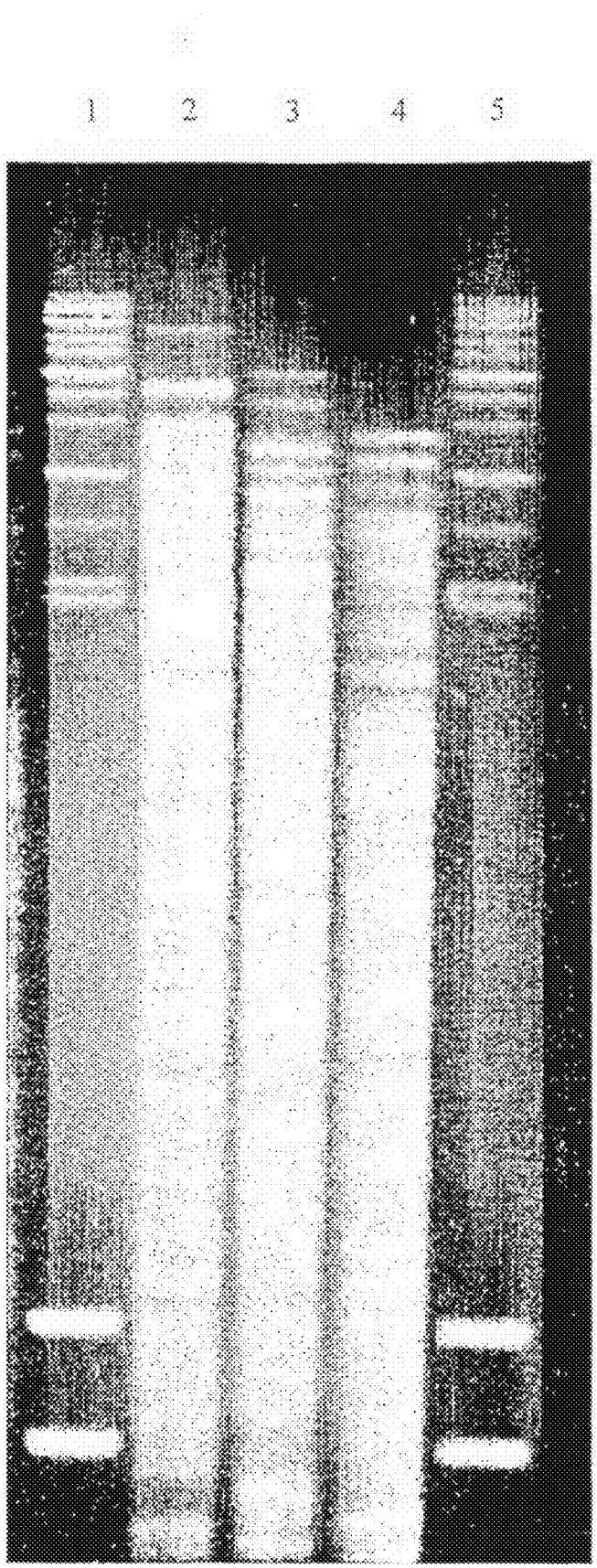
FIG. 4 shows separated DNA fragments obtained by cleaving chromosomal DNA of the strain *L. crispatus* VPC 177 with the restriction enzymes Hind III (lane 2), Cla I (lane 3), Eco RI (lane 4). Molecular Weight DNA Markers were used as standards (lanes 1 and 5).
Figure 5:
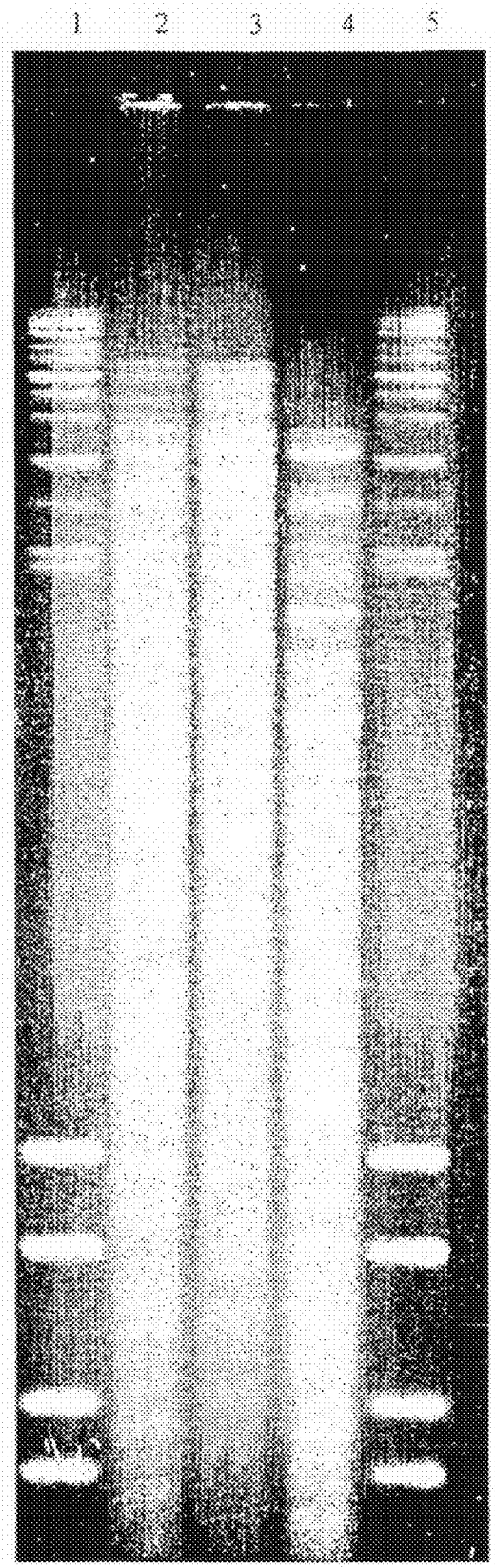
FIG. 5 shows separated DNA fragments obtained by cleaving chromosomal DNA of the strain *L. crispatus* VPC 5 with the restriction enzymes Hind III (lane 2), Cla I (lane 3), Eco RI (lane 4). Molecular Weight DNA Markers were used as standards (lanes 1 and 5).
Figure 6:
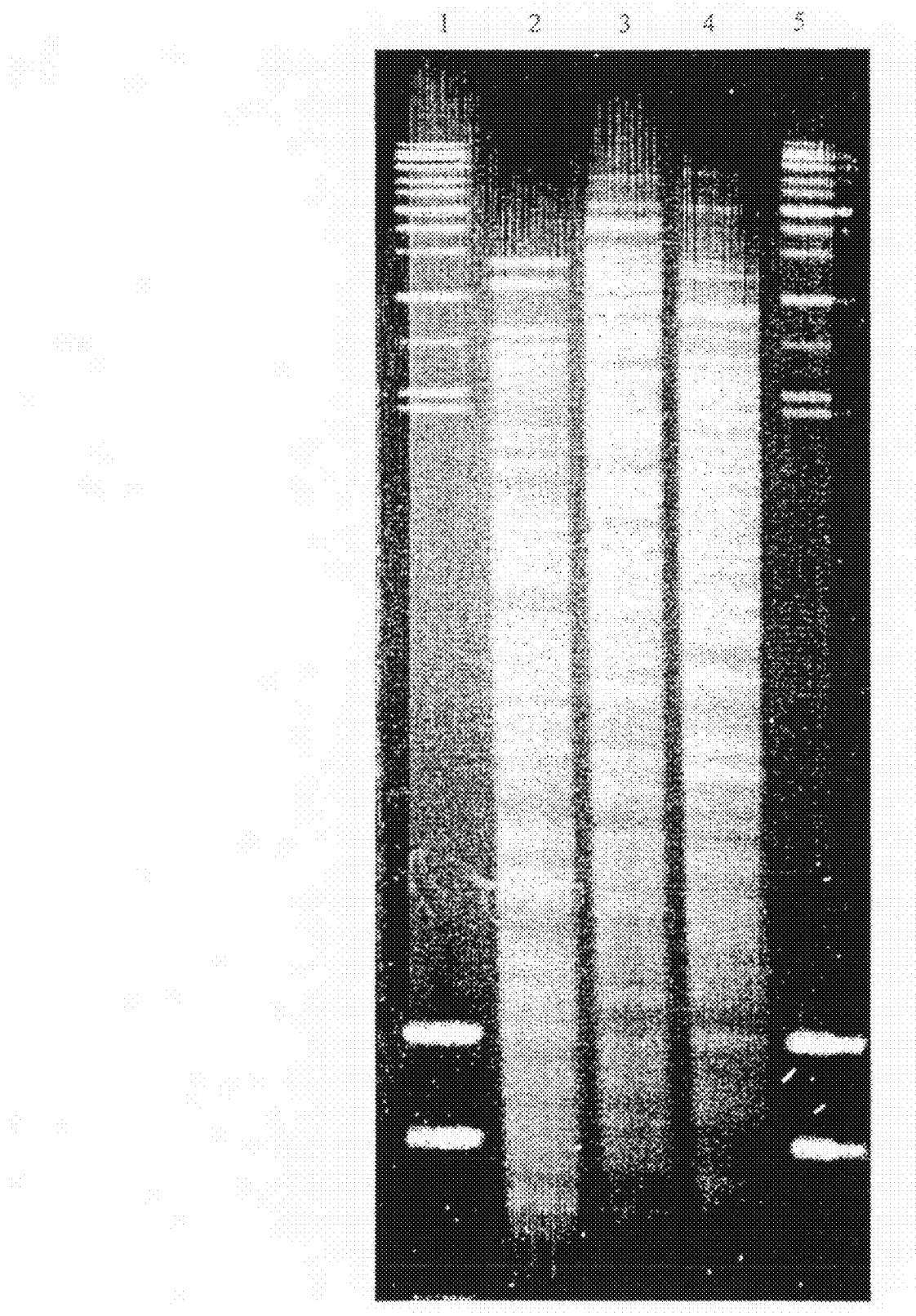
FIG. 6 shows separated DNA fragments obtained by cleaving chromosomal DNA of the strain *L. crispatus* VPC 40 with the restriction enzymes Hind III (lane 2), Cla I (lane 3), Eco RI (lane 4). Molecular Weight DNA Markers were used as standards (lanes 1 and 5).
Figure 7:
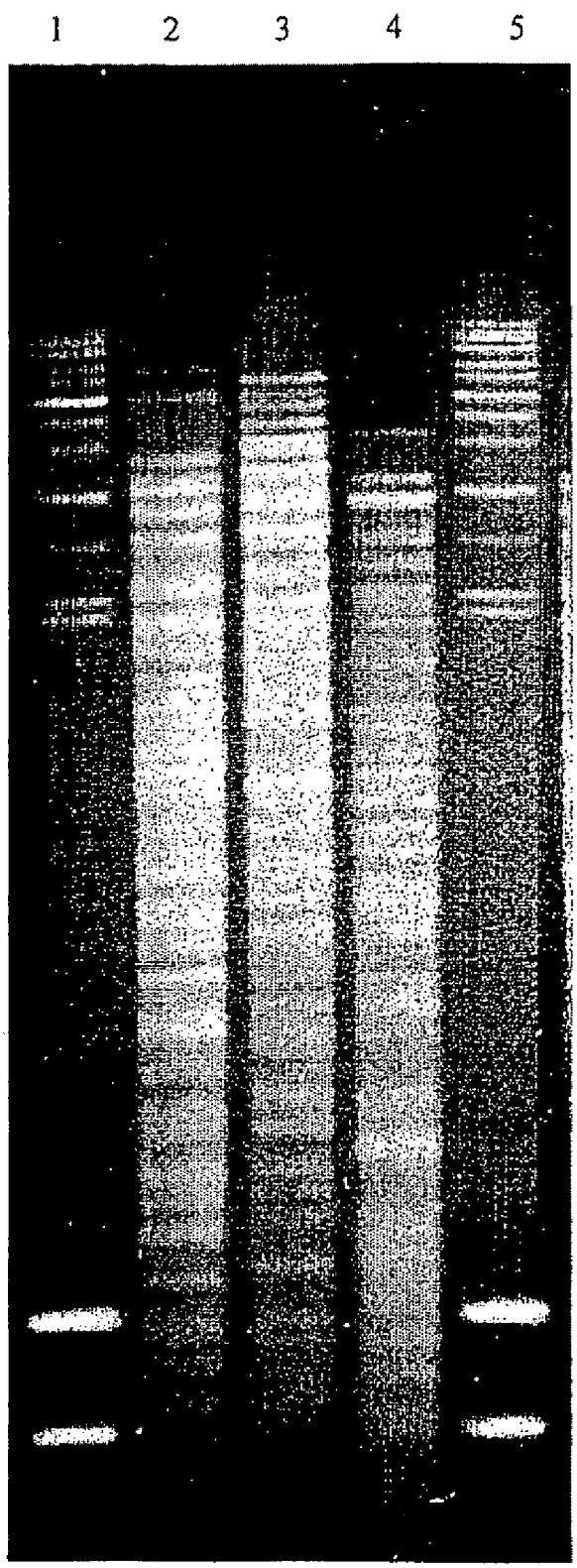
FIG. 7 shows separated DNA fragments obtained by cleaving chromosomal DNA of the strain *L. crispatus* VPC 71 with the restriction enzymes Hind III (lane 2), Cla I (lane 3), Eco RI (lane 4). Molecular Weight DNA Markers were used as standards (lanes 1 and 5).
Figure 8:
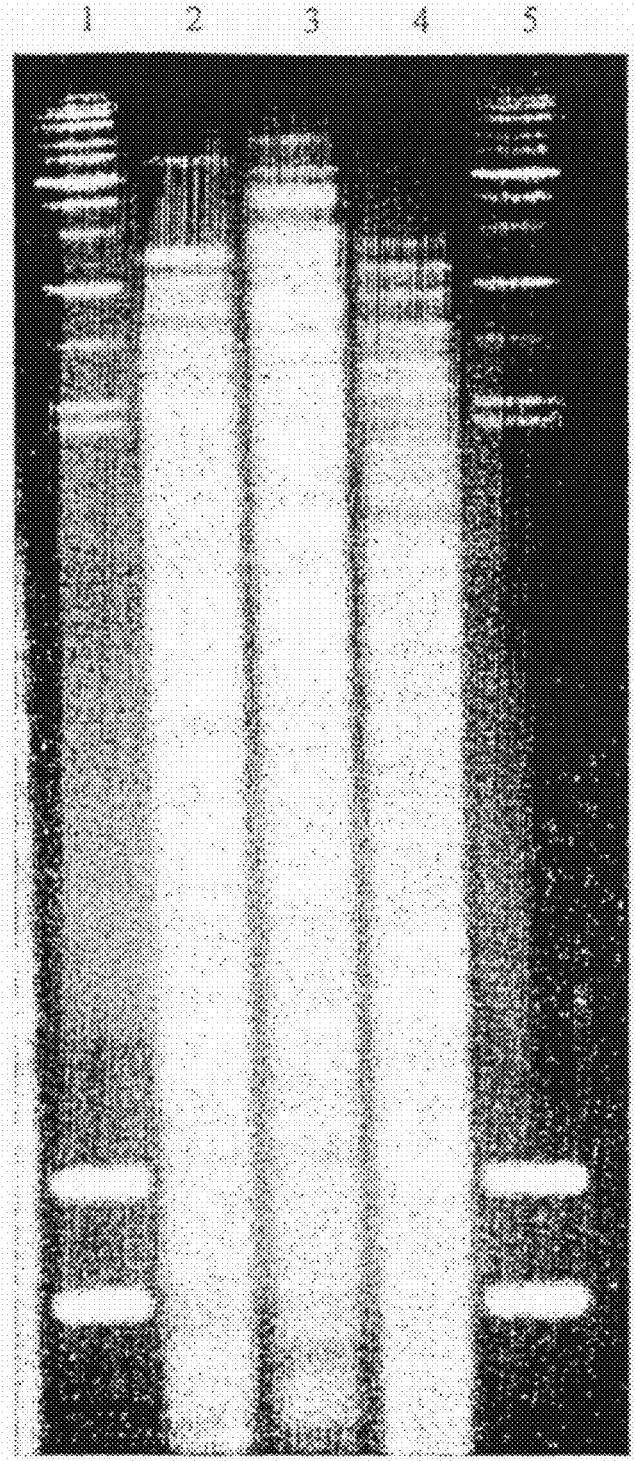
FIG. 8 shows separated DNA fragments obtained by cleaving chromosomal DNA of the strain *L. crispatus* VPC 111 with the restriction enzymes Hind III (lane 2), Cla I (lane 3), Eco RI (lane 4). Molecular Weight DNA Markers were used as standards (lanes 1 and 5).
Figure 9:
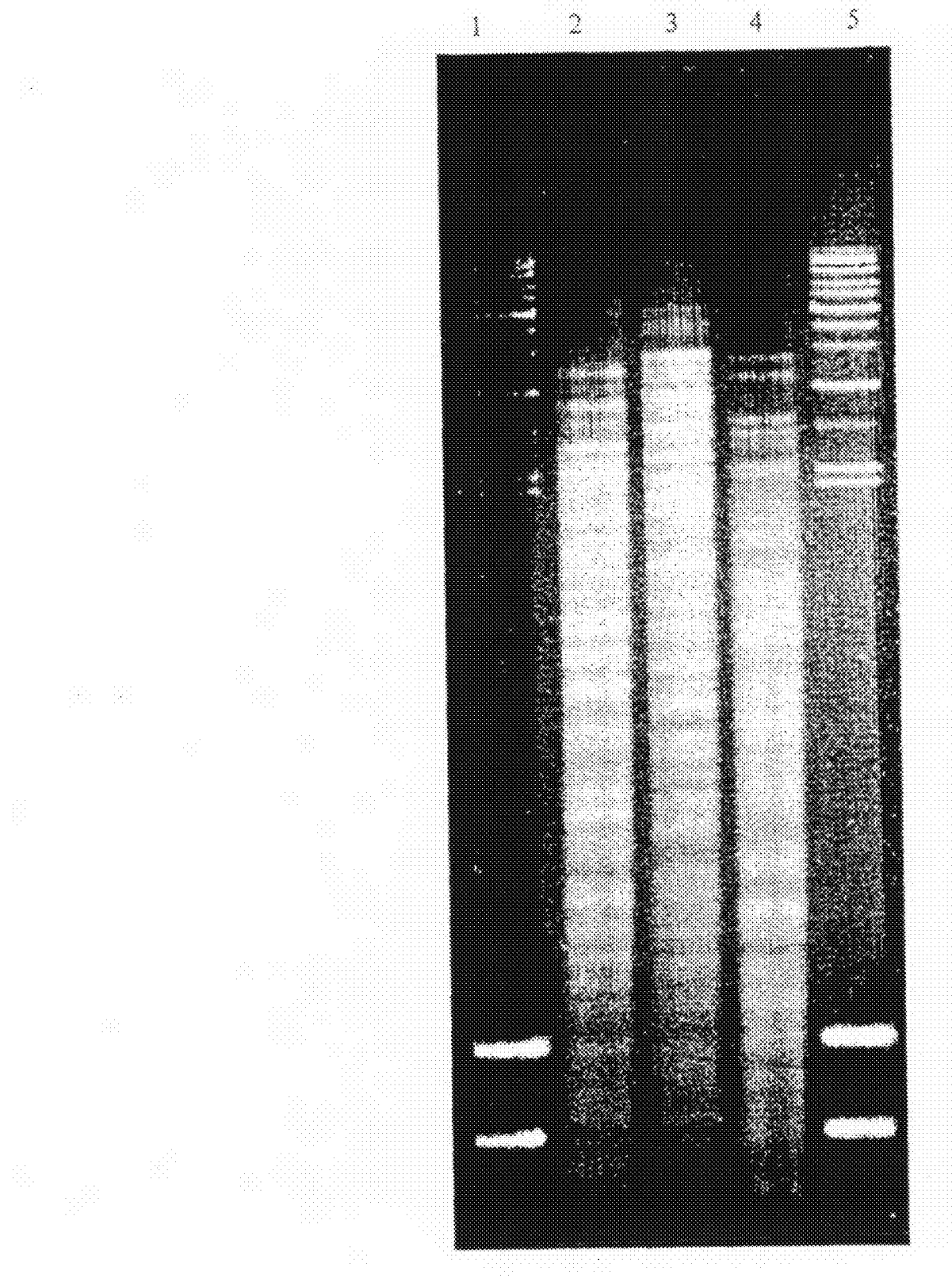
FIG. 9 shows separated DNA fragments obtained by cleaving chromosomal DNA of the strain *L. crispatus* VPC 130 with the restriction enzymes Hind III (lane 2), Cla I (lane 3), Eco RI (lane 4). Molecular Weight DNA Markers were used as standards (lanes 1 and 5).
Figure 10:
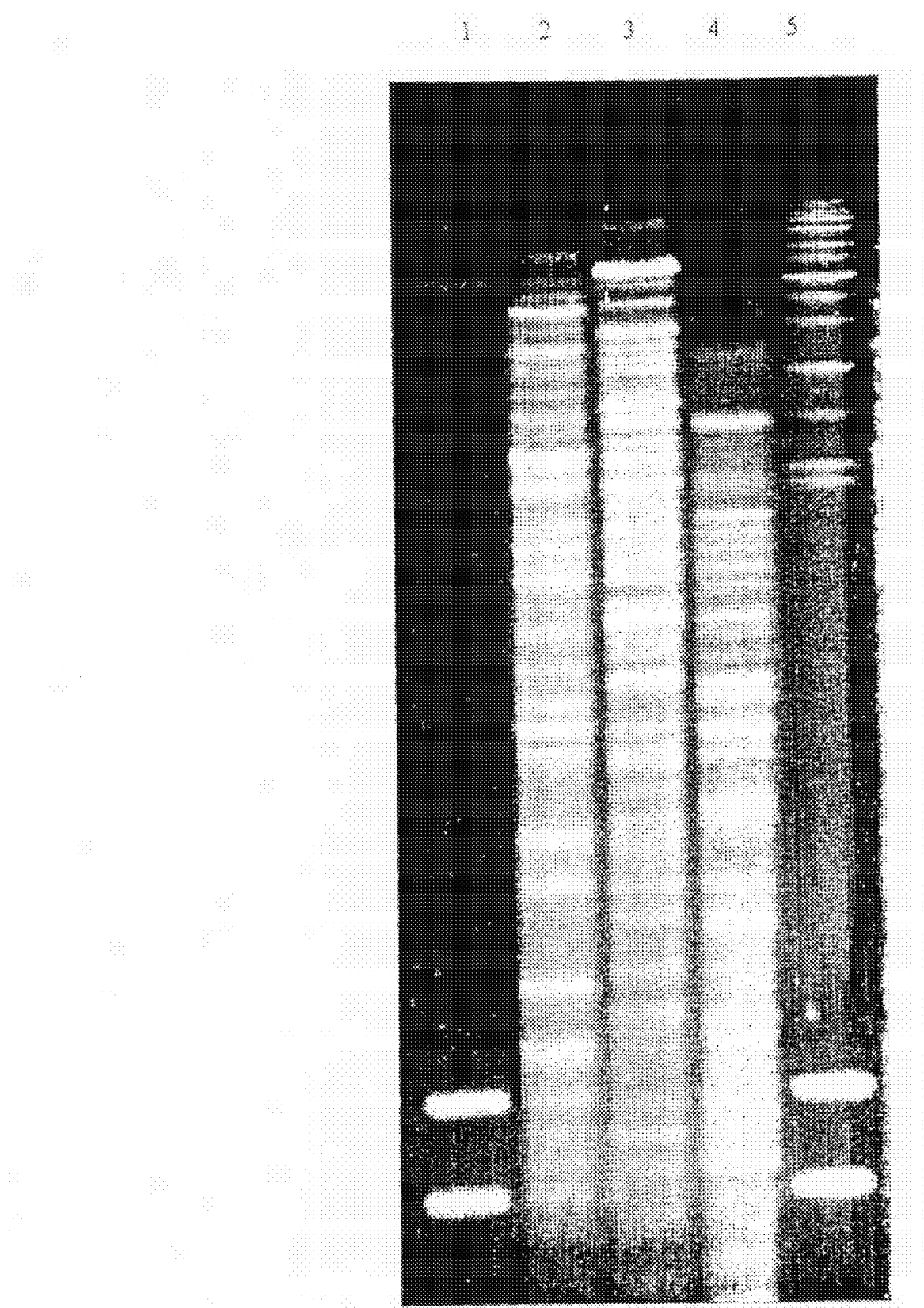
FIG. 10 shows separated DNA fragments obtained by cleaving chromosomal DNA of the strain *L. gasseri* VPG 44 with the restriction enzymes Hind III (lane 2), Cla I (lane 3), Eco RI (lane 4). Molecular Weight DNA Markers were used as standards (lanes 1 and 5).

The present invention refers inter alia to a composition comprising one or more strains of *Lactobacillus plantarum* or closely related *Lactobacillus* spp. with ability to colonize vagina via oral administration and intestinal establishment. Said composition will e g pre-serve vaginal health, attenuate vaginosis, yeast vaginitis, urinary tract infection, sexually transmitted diseases and infections that might endanger the foetus in pregnant women.

A healthy uro-genital micro-riora comprises >50 species of micro-organisms. Healthy uro-genital cells are covered by bacterial bio films where lactobacilli predominate. The healthy vagina is maintained by the interaction of the vaginal epithelium and the microbial flora. Pathogens in the faecal flora are the origin of urinary tract infection and bacterial vaginosis. One of the factors in pathogenesis is the ability of the pathogens to attach to epithelial cells. Adhesins and receptor sites are involved in this attachment process. For example the pathogen *E. coli* have a mannose-specific adhesion on epithelial surfaces. Some Lactobacilli have previously been shown to have a mannose-specific adhesion as well. By utilizing this mechanism some probiotic lactobacilli may also prevent pathogens from adhering to mucosal surfaces such as vaginal and urethral mucosa and thus prevent infection. Other factors are maintaining the low pH in the vagina by the glucose metabolism, production of hydrogen peroxide and bacteriocin-like production to suppress growth of pathogens and other unwanted microorganisms.

The invention especially refers to the strains *Lactobacillus crispatus* VPC5, deposition number DSM 16735, *Lactobacillus crispatus* VPC40, deposition number DSM 16736, *Lactobacillus crispatus* VPC70, deposition number DSM 16738, *Lactobacillus crispatus* VPC71, deposition number DSM 16739, *Lactobacillus crispatus* VPC77, deposition number DSM 16740, *Lactobacillus crispatus* VPC111, deposition number DSM 16741, *Lactobacillus crispatus* VPC130, deposition number DSM 16742, *Lactobacillus crispatus* VPC177, deposition number DSM 16743, and *Lactobacillus gasseri* VPG44, deposition number DSM 16737, which were deposited at the Deutsche Sammlung von Mikroorganismen und Zellkulturen GmbH on Sep. 17, 2004 and were then given the accession numbers referred to above, or variants thereof. Said strains having the ability to colonize the vagina.

The invention also refers to the use or the bacterial strains *Lactobacillus plantarum* HEAL 9, deposition number DSM 15312, *Lactobacillus plantarum* HEAL 19, deposition number DSM 15313, *Lactobacillus plantarum* HEAL 99, deposition number DSM 15316, which were deposited at the Deutsche Sammlung von Mikroorganismen und Zellkulturen GmbH on Nov. 27, 2002 and were then given the accession numbers referred to above, or variants thereof.

The invention also refers to the use of the bacterial strains *Lactobacillus plantarum* 299, deposition number DSM 6595, which were deposited on 2 Jul. 1991, and *Lactobacillus plantarum* 299v, deposition number DSM 9843, which were deposited on 16 Mar. 1995 at the Deutsche Sammlung von Mikroorganismen und Zellkulturen GmbH and were then given the accession numbers referred to above, or variants thereof.

The phrase "variant thereof" as used herein in reference to the bacterial strains of the invention, especially those which have been deposited, is defined as a bacteria

- belonging to the cluster having a RAPD similarity of at least 80% to said probiotic bacterial strain, by using the Pearson product moment correlation coefficient and the unweighted pair algorithm with arithmetic averages (UPGMA; BioNumerics 2.5, Applied Maths, Kortrijk, Belgium); and/or
- belonging to a cluster having a restriction endonuclease analysis similarity of preferably at least 75% to said probiotic bacterial strain, by using the Pearson product moment correlation coefficient and the unweighted pair algorithm with arithmetic averages (UPGMA; BioNumerics 2.5, Applied Maths, Kortrijk, Belgium); and/or
- having the ability to colonize the human vagina; and/or
- having a mannose-specific adhesin or other adhesive mechanisms that allow the bacteria to bind to the inner surface of the vagina, the gastro intestinal tract, urinary bladder including the urethra.

The phrase "probiotic bacterial strain(s)" as used herein in reference to the invention is meant live microorganisms which when administered in adequate amounts confer a health benefit on the host. In addition, when the bacterial strains are taken orally, the bacterial strains must survive the passage through the gastro-intestinal tract and, when the bacterial strains are taken vaginally or rectally, the bacterial strains must colonize the vagina and rectum, respectively.

The phrase "colonize the human vagina" as used herein in reference to the bacterial strains of the invention is meant that the viable count of lactobacilli (log cfu/swab) in the vaginal fluid and/or faeces is at least increased after taking the bacterial strain orally, rectally or vaginally compared to the total lactobacilli counts initially, i.e. before taking any of the bacterial strains.

DETAILED DESCRIPTION OF EMBODIMENTS OF THE INVENTION

Genotypic Identification by REA

The strains (Lactobacillus crispatus VPC5, deposition number DSM 16735, *Lactobacillus crispatus* VPC40, deposition number DSM 16736, *Lactobacillus crispatus* VPC71, deposition number DSM 16739, *Lactobacillus crispatus* VPC111, deposition number DSM 16741, *Lactobacillus crispatus* VPC130, deposition number DSM 16742, *Lactobacillus crispatus* VPC177, deposition number DSM 16743, and *Lactobacillus gasseri* VPG44, deposition number DSM 16737, were examined as to the cleavage pattern of the chromosomal DNA, through restriction-endonuclease analysis—REA—method according to Stahl M, Molin G, Persson A, Ahrné S & Ståhl S, International Journal of Systematic Bacteriology, 40:189-193, 1990, and further developed by Johansson, M-L, et al., International Journal of Systematic Bacteriology 45:670-675, 1995. Schematically REA can be described as follows: Chromosomal DNA from the strains involved in the study were prepared and cleaved by restriction endonucleases. 0.75 µg of each DNA was separately digested at 37° C. for 4 h with 10 units of Hind III, Cla I and EcoRI; each endonuclease was used separately. The cleaved DNA fragments are separated as to size by gel electrophoresis using submerged horizontal agarose slab gels. The gels consisted of 150 ml of 0.9% agarose (ultrapure DNA grade; low electroendo osmosis; BioRad Laboratories, Richmond, USA) and were cast as slab gels (150 by 235 mm). 0.2 µg of the High Molecular Weight DNA marker (Bethesda Research Laboratories, Md., USA) together with 0.5 µg of a DNA molecular weight marker VI (Roche, Germany) were used as standards. Minimal band distortion and maximal sharpness were achieved by applying the sample DNA in Ficoll loading buffer (2 g of Ficoll, 8 ml of water, 0.25% bromphenol).

Gels were run at a constant voltage of 40V for 18 h at about 6-8° C. The buffer (89 mM Tris, 23 mM $H_3PO_4$, 2 mM sodium EDTA, pH 8.3) was recirculated during the running period. Thereafter, the gels were stained for 20 minutes in ethidium bromide (2 µg/ml) and destained in distilled water, visualized at 302 nm with a UV transilluminator (UVP Inc., San Gabriel, USA) and photographed. This way of running the gel electrophoresis gave well distributed and relatively well-separated band down to a molecular weight of $1.2 \times 10^6$.

The results of the analysis are presented in the FIGS. 4-10.

Example 1

Volunteers and Strains

Ten healthy women at different ages with no vaginal infections or any intestinal diseases participated in the study. The study subjects provided information about their age, menstrual cycle and health behavior by a questionnaire. One week before the first samples were taken the volunteers had a washout period in which they avoided all kind of probiotic containing formulas.

The bacterial strains used in the study are presented in Table 1. They were chosen among a battery of 23 *Lactobacillus* after qualities such as Viable Count numbers after culturing in the laboratory, fermentation of oat meal gruel and ability to withstand freezing and thawing.

Twelve of the most resistant strains were selected for administration to the volunteers; bacterial concentration and incubation time for culture are given in Table 1. The administration was performed during 10 days. The bacterial strains were prepared from a fresh culture in LCM (Lactobacillus carrying medium) (Efthymiou C, Hansen C A. An antigenic analysis of *Lactobacillus acidophilus*. J Infect Dis 1962; 110: 258-267). Cells of each culture equivalent a concentration of about $10^9$ bacteria in a total volume of 100 ml were harvested by centrifugation and washed once in Millipore—$H_2O$. The pellets were then dissolve in 20 ml oat milk (Beneviva, Finland) and 80 ml blueberry soup (Ekströms, Sweden), which was the drink administrated to the subjects.

TABLE 1

Selected bacterial *Lactobacillus* (L.) strains for the administration.

| Bacterial species | Strain number | Source (human) | Administration conc. ($\times 10^9$) | Incubation time (d) |
|---|---|---|---|---|
| L. crispatus | VPC77 | vagina | 1.1 | 2 |
| L. crispatus | VPC111 | vagina | 1.0 | 2 |
| L. crispatus | VPC130 | vagina | 2.7 | 2 |
| L. crispatus | VPC5 | vagina | 1.2 | 2 |
| L. crispatus | VPC40 | vagina | 1.3 | 2 |
| L. crispatus | VPC70 | vagina | 1.6 | 2 |
| L. crispatus | VPC71 | vagina | 1.1 | 2 |
| L. crispatus | VPC177 | vagina | 1.6 | 2 |
| L. gasseri | VPG44 | vagina | 1.1 | 1 |
| L. plantarum | HEAL19 | intestinal mucosa | 1.3 | 1 |
| L. plantarum | HEAL9 | intestinal mucosa | 2.2 | 1 |
| L. plantarum | HEAL99 | intestinal mucosa | 1.2 | 1 |

Sample Collection

The volunteers delivered faecal and vaginal fluid samples that were cultivated on agar plates within 3 hours after the delivery to the laboratory. The sampling was at the beginning of the treatment (T0), after 10 days of administration (T1) and 7 days after termination of the administration (T2).

Vaginal samples were taken by inserting a vaginal swab (Copan amies agar gel swabs; Copan innovation, Italy) trough a cap to prevent bacterial contamination. The vaginal swabs were agitated in 9 ml sterile phosphate-buffered saline (PBS) pH 7.2 and serially diluted. One gram faeces were agitated in 9 ml PBS and serially diluted. Aliquots of each dilution for the vaginal samples and the last three dilutions for the faecal samples were plated on Rogosa agar (Oxoid AB, Sollentuna, Sweden) and anaerobically incubated during 3 days in a BBL Gas Pack system at 37° C.

Six colonies from both faecal and vaginal samples were randomly picked after the incubation. Moreover, colonies with typical morphological appearance were searched for and additionally picked when found.

Strain Typing

Totally 338 isolates were grouped using Randomly Amplified Polymorphic DNA (RAPD) together with the administrated strains. They were cultivated again in Rogosa agar (Oxoid) to verify that they were free from contamination.

The primer used in the PCR-amplification was a 9-mere with the sequence 3'-ACG CGC CCT-5' (Scandinavian Gene Synthesis AB, Köping, Sweden). The following PCR-amplification and agarose gel electrophoresis was performed, as previously described by Quednau M, Ahrné S, Pettersson A C, Molin G. Identification of clinically important species of *Enterococcus* with in 1 day with Random Amplified Polymorphic DNA (RAPD) Curr. Microbiol. 1998; 36: 332-6. One µl of PCR-templates were used in a total reaction volume of 50 µl containing PCR-buffer with 1.5 mM $MgCl_2$ (Roche Diagnostics GmbH, Mannheim, Germany), 0.2 mM of each nucleotide (Roche) and 2.5 units of Taq DNA polymerase (Roche). The PCR amplification was according to the following temperature profile: 94° C. for 45 s, 30° C. for 120 s, 72° C. for 60 s, for four cycles followed by 94° C. for 5 s, 36° C. for 30 s (with extension of 1 s for each cycle), 72° C. for 30 s, for 26 cycles. The PCR session concluded with 72° C. for 10 minutes, followed by cooling to 4° C. The products were visualized by agarose gel electrophoresis and photo-negatives of RAPD-gels were scanned by a Hewlett Packard ScanJet 5300C into a computer at a resolution of 300 dpi. The gel images were then analyzed and grouped by GelCompar 4.2 (Applied Maths, Kortrijk, Belgium) with Pearson product moment correlation coefficient (r) and the unweighted pair group method by arithmetic averages (UPGMA).

Strain Identification

REA-Restriction Endonuclease Analysis

Thirty-six isolates together with the administrated strains were selected from the RAPD-grouping and further identified by REA (Restriction Endonuclease Analysis) to assure the presence of the exogenous strains in the faecal and vaginal samples of the subjects.

Preparation of Chromosomal DNA was Carried Out as a procedure described previously (Ulrich R L, Hughes T A. A rapid procedure for isolating chromosomal DNA from *Lactobacillus* species and other gram-positive bacteria. Lett Appl Microbiol 2001; 32: 52-56). Gel electrophoresis was according to an earlier protocol by Johansson et al. (Johansson M L, Quednau M, Ahrné S, Molin, G. Classification of *Lactobacillus plantarum* by restriction endonuclease analysis of total chromosomal DNA using conventional agarose gel electrophoresis. Int J Syst Bacteriol 1995; 45: 670-5).

DNA (0.75 µg) was separately digested at 37° C. for 4 h with 10 units of HindIII and EcoRI (Roche). Submerged horizontal 0.9% agarose (High Strength Analytical Grade Agarose: low electro-endo osmosis, Bio-Rad Laboratories, Calif., USA) slab gels in size of 150 by 235 mm were used. Amounts of 0.2 µg of a high molecular weight DNA marker (Gibco, Invitrogene Corporation, Sweden) together with 0.5 µg of a DNA molecular weight marker VI (Roche) were used as standards. Gels were run at a constant voltage of 40 V for 18 h at 5° C. Thereafter, the bands were visualized at 302 nm with a UV transilluminator (UVP Inc., San Gabriel, Calif., USA) and photographed.

Results

Five of the administrated strains were recovered from 8 of the 10 subjects, both after the 10 days treatment (T1) and 1 week after that the administration ended (T2). The re-isolated strains at T1 were *L. crispatus* VPC177, *L. gasseri* VPG44 and *L. plantarum* HEAL 19; whereas *L. plantarum* HEAL 99 and *L. plantarum* HEAL 9 were recovered both at T1 and T2 (Table 2).

TABLE 2

Re-isolated strains found in vaginal and faecal samples of subjects (S). "d" within parenthesis indicates that the strain was re-isolated from a randomly picked colony, i.e. the strain represented a dominating part of the total *lactobacilli* flora.

| Strain | Subject number | Sampling time T1 | T2 |
|---|---|---|---|
| L. crispatus VPC177 | S7 | faeces | — |
| L. gasseri VPG44 | S2 | faeces | — |
| | S10 | faeces (d)* | — |
| L. plantarum HEAL 19 | S3 | faeces (d) | — |
| | S4 | faeces | — |
| | S5 | faeces (d); | — |
| | S6 | vagina | — |
| | S7 | faeces (d) | — |
| | S8 | faeces (d); | — |
| | S9 | vagina (d) | — |
| | S10 | faeces (d) faeces vagina (d) | — |
| L. plantarum HEAL 99/9 | S3 | faeces (d) | vagina (d) |
| | S4 | — | vagina (d) |
| | S7 | faeces (d) | — |
| | S9 | faeces (d) | — |
| | S10 | faeces (d) | — |

RAPD—Randomly Amplified Polymorphic DNA (RAPD)

The most interesting bacterial strains were also analyzed with the PCR-based method of Randomly Amplified Polymorphic DNA (RAPD) as described by Johansson et al 1995 Randomly Amplified Polymorphic DNA (RAPD) for rapid typing of *Lactobacillus plantarum* strains. Lett. Appl. Microbiol. 21:155-159, with the following modifications. Crude cell extracts were prepared from 3-5 colonies of a pure culture from MRS agar plates. The cells of pure culture were washed twice in 1 ml sterile Milli-Q water, and disrupted in an Eppendorf tube with glass beads (2 mm in diameter) using an Eppendorf Mixer (5432; Eppendorf, Hamburg Germany) for 10 minutes. The primer used had the sequence 5'-CCG-CAGCCAA-3' (SEQ ID NO.: 1) and a concentration of 15 µM. Taq mastermix from Qiagen was used in the PCR reaction. The band patterns for the gels were analyzed with Pearson product moment correlation coefficient (r) and the Unweighted Pair Group Method with Arithmetic averages (UPGMA; Romersburg, 1984) by using BioNumerics 2.5 (Applied Maths, Kortrijk, Belgium). The computerized cluster analysis of the RAPD-patterns was combined with a visual comparison.

By using the RAPD method described above on the eight *L. crispatus* strains and one *L. gasseri* strain of table 1 two clusters containing strains with an 80% similarity could be identified (see the dendrogram of figure 1). Strains within such a cluster are regarded as variants of each other and predicted to have similar properties. One of the clusters contains the strains VPC 70, VPC 71 and VPC 5 and the other contains strains VPC 177, VPC 40 and VPC 111. Strain VPC 177 for example could be found in the vagina after oral administration and it is therefore likely other strains within the same RAPD cluster also have the ability to do so.

Conclusion

The experiment demonstrates an unexpected ability of the chosen *L. plantarum* strains to colonize the vagina via oral administration and intestinal establishment. It should be pointed out that the results is achieved with relatively low doses of probiotics administered for short times and that the *L. plantarum* strains were compared with strains more typical for the vagina, i.e. more frequently occurring species and strains isolated from vagina.

Example 2

Yeast Agglutination as a Measure of Mannose Adhesion

In this experiment the ability of the bacteria to agglutinate yeast cells were determined by eye as visible precipitation of yeast cells and bacteria. Washed bacteria were suspended at a concentration of $2\times10^{10}$ cells per ml in PBS (pH 7.2). A solution of 2.5% (wt/vol) baker's yeast (*Saccharomyces cerevisiae*) suspended in PBS or 0.125% (wt/vol) D-Mannose containing PBS were added to a equal volume of bacterial solution on a microscope slide. The bacteria and the yeast solutions were mixed by gentle rocking of the slide and the number of turns were calculated until a precipitation of agglutinated yeast and bacterial cells appeared. This number of turns was compared between the solution with and without mannose. The yeast agglutination was classified as mannose sensitive if the number of turns until visible precipitation appear differ more than ten times between the samples with or without mannose.

During the experiment it was shown that *Lactobacillus crispatus* VPC 177 and VPC 70 have the ability to agglutinate yeast in a mannose sensitive manner. Mannose sensitive yeast agglutination has previously been shown to correlate with the ability to adhere to cells of the human colonic carcinoma cell line HT-29. (Adlerberth, I., Ahrné, S., Johansson, M-L., Molin, G., Hanson, L-Å., and Wold, A. E. (1996). A mannose-specific adherence mechanism in *Lactobacillus plantarum* conferring binding to the human colonic cell line HT-29, *Appl. Environ. Microbiol.*, 62, 2244-2251.), and is thus a factor promoting the colonization and persistence of the bacteria in question in the intestine. Therefore, it is with high probability likely true that this feature of the bacteria also is of importance for colonisation in the vagina and urinary tract, and thereby a mechanism to compete with uropathogenic bacterial strains of *Escherichia coli*. This feature, thus a mannose-specific adherence mechanism, has previously also been shown for *Lactobacillus plantarum* 299, deposition number DSM 6595, and *Lactobacillus plantarum* 299v, deposition number DSM 9843.

Example 3

The aim of the experiment below was to investigate the establishment of 4 *Lactobacillus* strains in the intestines and vagina by studying its presence in faeces and vaginal fluid following the intake of the lactic acid bacteria in a freeze dried formula orally.

It is important to emphasize that the experiment is carried out in vivo in humans, as neither in vitro studies nor animal studies would reflect the degree of survival when administered to humans. The ability of these bacteria to become established in the intestine when administered directly after cultivation is documented in an earlier study (Moreno, Alejandra Vasquez 2004 PhD thesis: Systematics of *Lactobacillus* spp. of probiotic potential Food Technology; Lund University.). In said study fresh bacterial cells from overnight cultivation were used. However, it would be more convenient to use a lyophilized product in a real product. Therefore, a lyophilized formulation has been chosen for that reason in this experiment.

The primary objective was to investigate the presence in faeces and vaginal fluid of four *Lactobacillus* strains, originating from vagina, following oral ingestion of the strains in an open study.

Since many diseases in the vagina such as urinary tract infection arise from the rectal mucosa it is beneficial to see an increase in viable count of healthy lacotbacilli in both faeces and vaginal fluid. If the healthy bacterial strains of the invention affect rectum in addition to the vagina, the healthy lactobacilli bacteria of the invention will suppress the non-desirable bacteria in rectum, thereby avoiding diseases in the vagina ascending from rectum.

Materials and Methods

Experiment Design

The experiment was an open study and was carried out on one group of subjects. The experiment was divided into eight periods:
1. A wash-out period of 14 days (day 1-14)
2. An ingestion period of *Lactobacillus* crispatus VPC 111 during 14 days orally (day 15-28).
3. A wash-out period of 14 days (day 29-42)
4. An ingestion period of *Lactobacillus gasseri* VPG 44 during 14 days orally (day 43-56).
5. A wash-out period of 14 days (day 57-70)
6. An ingestion period of *Lactobacillus* crispatus VPC 177 during 14 days orally (day 71-84).
7. A wash-out period of 14 days (day 85-98)
8. An ingestion period of *Lactobacillus plantarum* HEAL 9 during 14 days orally (day 99-112).

Subjects and Recruitment

36 Healthy women aged 18-65 years were recruited by sending out information to the employees at Ideon and Chemical Centre (Lund University) in Lund. Employees of Probi AB, known intolerance or allergy to any ingredient included in the formulations, current treatment for severe gastrointestinal disorders and current treatment for vaginal disorders were excluded.

The experimental products contained lyophilized *Lactobacillus crispatus* VPC177, *Lactobacillus crispatus* VPC 111, *Lactobacillus plantarum* HEAL9 and *Lactobacillus gasseri* VPG44, respectively. Sucrose, maltodextrine and hydrolysed gelatine were added as cryoprotectants.

The daily intake was 2×1 g lyophilized lactobacilli (approximately $1 \times 10^9$ cfu/day) orally. The doses were taken morning and evening and were to be ingested in association with a meal. The product was supplied in sachets.

Dietary Regulations

From day 1 to day 113, the subjects were not allowed to ingest products containing probiotic bacteria. Each subject was provided with a list of probiotic products not allowed to be consumed during the study period. This was done in order to secure that other probiotic bacteria could not interfere with the experiment.

Concomitant Medication

All concomitant medication was to be noted on the Case Report Form (CRF) and in the diary.

Exclusion criteria during the study were subjects who had not taken >4 doses (2 days) in succession or have not taken a total of >8 doses (4 days) during each ingestion period of the study, subjects who had not followed the dietary regulations, subjects who had started a course of medical treatment for severe gastrointestinal disease between day 1 and day 112 (on the discretion of the principal investigator), and subjects who wished to discontinue the study.

Faecal and vaginal samples were handed in on days 15, 29, 43, 57, 71, 85, 99 and 113. The sample on day 15, 43, 71 and 99 was collected before taking the first dose of the periods experiment product. The samples were collected no more than 18 hours before being handed in for analysis, and during this period stored in a refrigerator. The samples were analyzed for lactobacilli.

Vaginal samples was collected by inserting a vaginal swab (Copan amies agar gel swabs; Copan innovation, Brescia, Italy) through a cap to prevent bacterial contamination. The samples were collected no more than 3 hours before being handed in for analysis, and during this period stored in a refrigerator.

The samples were analyzed microbiologically (according to Johansson et al., 1998) with regard to the lactobacilli flora. (Rogosa agar, anaerobically, 3 days at 37° C.) The different lactobacilli were identified with Randomly Amplified Polymorphic DNA analysis (RAPD) according to Johansson et al., Lett. Appl. Microbiol. 1995; 21: 155-159.

The statistical values were calculated according to Wilcoxon signed ranks test, see table 1 and 2.

Results

Of the 36 women included 31 participated in period 1 and 2 (WO+VPC111), 34 in period 3 and 4 (WO+VPG44), 28 in period 5 and 6 (WO+VPC177) and 31 in period 7 and 8 (HEAL 9). 25 of the women participated in all of the study periods.

TABLE 1

*Lactobacilli* (mean (min-max)) in faecal samples before and after 2 weeks intake of experimental product. Values under detection level are set to 3.0 and values over detection level are set to 9.0 to enable calculation.

|  | Faecal counts (cfu/g) | |
| --- | --- | --- |
| Strain in exp product | Total lactobacilli | Administered exp. strain |
| VPC111 | | |
| Before intake | 4.9 (<3-7.3) | 3.0 (<3-4.6) |
| After intake | 6.2 (<3->9) | 3.0 (<3) |
|  | p = 0.01 | |
| VPG44 | | |
| Before intake | 5.8 (<3->9) | 3.0 (<3-4.2) |
| After intake | 6.1 (3.8-8.7) | 3.3-(<3-5.9) |
| VPC177 | | |
| Before intake | 5.4 (<3.0-9.0) | 3.1 (<3-4.5) |
| After intake | 7.0 (<3.0-9.8) | 3.3 (<3-8.1) |
|  | p = 0.000 | |
| HEAL9 | | |
| Before intake | 6.9 (<3->9) | 3.0 (<3) |
| After intake | 7.2 (4.0-9.4) | 5.8 (<3-8.0) |
|  | | p = 0.000 |

TABLE 2

*Lactobacilli* (mean (min-max)) in vaginal samples before and after 2 weeks intake of experimental product. Values under detection level are set to 2.0 for vaginal samples to enable calculation.

|  | counts (log cfu/swab) | |
| --- | --- | --- |
| Strain in exp. product | Total lactobacilli | Administered exp. strain |
| VPC111 | | |
| Before intake | 5.0 (<2-8.2) | 2.0 (<2-4.6) |
| After intake | 4.9 (<2-8.0) | 2.3 (<2-7.3) |
| VPG44 | | |
| Before intake | 5.1 (<2-8.8) | 2.0 (<2) |
| After intake | 5.2 (<2-8.4) | 2.0 (<2) |
| VPC177 | | |
| Before intake | 4.7 (<2-8.0) | 2.2 (<2-6.6) |
| After intake | 5.3 (<2-8.2) | 2.2 (<2-7.2) |
|  | p = 0.03 | |
| HEAL9 | | |
| Before intake | 5.4 (<2-8.3) | 2.0 (<2) |
| After intake | 5.3 (<2-8.5) | 2.1 (<2-4.2) |

The two strains of *Lactobacillus crispatus* VPC111 and VPC177 caused significant increases of total lactobacilli in faecal flora. In addition significant increases in total lactobacilli in vaginal fluid were observed after intake of VPC177 orally. Thus, it is very interesting to note that after taking the probiotic bacteria *Lactobacillus crispatus* VPC111 and VPC177 orally a total increase of the lactobacilli in faeces is observed. A significant increase of total Lactobacilli is also observed in vaginal fluid after taking *Lactobacillus crispatus* VPC177 orally. Thus, it is not necessary to achieve beneficial effects in the vagina or rectum in terms of healthy Lactobacilli by taking the strain in a suppository or vaginal insert. It has now been shown that intake of certain Lactobacilli, such as crispatus VPC111 and VPC177, orally leads to a total increase of lactobacilli in faeces as well as in vaginal fluid.

The lack of effect from *L. plantarum* HEAL9 on both faecal and vaginal flora could be due to the high initial concentration of total lactobacilli. It could be speculated that the wash-out period after intake of VPC177 was not long enough (FIGS. 1 and 2). However, it is worth noting that in 27 women out of 31, *L plantarum* HEAL 9 could be recovered by Randomly Amplified Polymorphic DNA analysis (RAPD) according to Johansson et al., Lett. Appl. Microbiol. 1995; 21: 155-159. The other experimental strains were also recovered in women tested by (RAPD) after the intake.

In conclusion, the significant increase of total lactobacilli concentration in faeces and vaginal fluid indicates that the Lactobacilli were active and established. Since no other probiotic material was supplied during each intake period it must be the taken probiotic bacterial strain that achieves the effect.

Thus, vaginal lactobacilli strains, i.e. strains that have been isolated from the vagina originally, can survive the passage through the gastrointestinal tract via a lyophilised product taken orally and are able to re-colonize the vagina. *Lactobacillus* crispatus VPC177 in particular increases the total concentration of lactobacilli in vagina. This is very surprising since it is known that the stability of isolated vaginal Lactobacilli strains is very low due to a very high sensitivity. To increase the beneficial effects of the bacterial strains of the invention in terms of vaginal health, administration of the bacterial strain both orally and vaginally will help the vagina to stay healthy even more.

deposited as DSM 16743, and *Lactobacillus gasseri* VPG44, which is deposited as DSM 16737.

2. The probiotic bacterial strain according to claim 1, wherein said probiotic bacterial strain is viable.

3. A composition comprising:
(a) at least one isolated probiotic bacterial strain selected from the group consisting of *Lactobacillus crispatus* VPC5, which is deposited as DSM 16735, *Lactobacillus crispatus* VPC40, which is deposited as DSM 16736, *Lactobacillus crispatus* VPC70, which is deposited as DSM 16738, *Lactobacillus crispatus* VPC71, which is deposited as DSM 16739, *Lactobacillus crispatus* VPC77, which is deposited as DSM 16740, *Lactobacillus crispatus* VPC111, which is deposited as DSM 16741, *Lactobacillus crispatus* VPC130, which is deposited as DSM 16742, *Lactobacillus crispatus* VPC177, which is deposited as DSM 16743, and *Lactobacillus gassed* VPG44, which is deposited as DSM 16737; and
(b) optionally, at least one isolated probiotic bacterial strain selected from the group consisting of *Lactobacillus plantarum* HEAL 9, which is deposited as DSM 15312, Lactobacillus plantarum HEAL 19, which is deposited as DSM 15313, and *Lactobacillus plantarum HEAL* 99, which is deposited as DSM 15316.

4. The composition according to claim 3, wherein said composition further comprises a carrier material.

5. The composition according to claim 3, wherein said composition is a food product.

6. The composition according to claim 3, wherein said composition is a food supplement.

7. The composition according to claim 4, wherein said carrier material is selected from the group consisting of oat meal gruel, lactic acid fermented foods, resistant starch, dietary fibers, inulines, carbohydrates, proteins and glycolsylated proteins.

8. The composition according to claim 5, wherein said food product is selected from the group consisting of bread, cheese, yogurt, juice, health bars, spreads, biscuits and cereals.

The invention claimed is:

1. An isolated probiotic strain selected from the group consisting of *Lactobacillus crispatus* VPC5, which is deposited as DSM 16735, *Lactobacillus crispatus* VPC40, which is deposited as DSM 16736, *Lactobacillus crispatus* VPC70, which is deposited as DSM 16738, *Lactobacillus crispatus* VPC71, which is deposited as DSM 16739, *Lactobacillus crispatus* VPC77, which is deposited as DSM 16740, *Lactobacillus crispatus* VPC111, which is deposited as DSM 16741, *Lactobacillus crispatus* VPC130, which is deposited as DSM 16742, *Lactobacillus crispatus* VPC177, which is 9. The composition according to claim 4, wherein said at least one probiotic bacterial strain is encapsulated or coated.

10. The composition according to claim 4, wherein said at least one probiotic bacterial strain is present in an amount giving, when consumed, an effective daily dose of $10^7$ to $10^{12}$ CFU.

11. The composition according to claim 3, wherein said composition is a pharmaceutical composition.

12. The composition according to claim 11, wherein said composition is administered orally, vaginally or rectally, or instilled into the urinary bladder.

13. The composition according to claim 11, wherein said composition is administered in a combined treatment of orally and vaginally, orally and rectally, or orally, vaginally and rectally.

14. The composition according to claim 11, wherein said carrier material is at least one pharmaceutically acceptable carrier.

15. The composition according to claim 11, wherein said composition is administered in a form selected from the group consisting of tablets, sucking tablets, sweets, chewing gum, capsules, enterocoated tablets and capsules, suppositories, micro-enemas, vaginal tablets, vaginal gelatin capsules, vaginal troches, cream, gel, ointment, lotion, tampons, napkins, pads, melting strips, condoms, pessaries, sprays and clinical nutrition products.

16. The composition according to claim 11, wherein said composition is administered orally, and wherein said at least one probiotic bacterial strain is present in an amount giving an effective daily dose of from $10^7$ to $10^{12}$ CFU.

17. The composition according to claim 11, wherein said composition is administered vaginally or rectally, and wherein said at least one probiotic bacterial strain is present in an amount giving an effective daily dose of from $10^3$ to $10^{12}$ CFU.

18. The composition according to claim 11, wherein said at least one probiotic bacterial strain is encapsulated or coated.

19. The composition according to claim 3, wherein said composition further comprises additives selected from the group consisting of vitamins, minerals and probiotics.

20. A hygiene product comprising a composition according to claim 3.

21. The hygiene product according to claim 20, wherein said hygiene product is selected from the group consisting of tampons, sanitary napkins, sanitary pads, diapers, soaps, shampoos, gels, ointments, creams, sprays and lotions.

22. A biological culture comprising:
(a) at least one isolated probiotic bacterial strain selected from the group consisting of *Lactobacillus crispatus* VPC5, which is deposited as DSM 16735, *Lactobacillus crispatus* VPC40, which is deposited as DSM 16736, *Lactobacillus crispatus* VPC70, which is deposited as DSM 16738, *Lactobacillus crispatus* VPC71, which is deposited as DSM 16739, *Lactobacillus crispatus* VPC77, which is deposited as DSM 16740, *Lactobacillus crispatus* VPC111, which is deposited as DSM 16741, *Lactobacillus crispatus* VPC130, which is deposited as DSM 16742, *Lactobacillus crispatus* VPC177, which is deposited as DSM 16743, and *Lactobacillus gasseri* VPG44, which is deposited as DSM 16737; and
(b) optionally, at least one isolated probiotic bacterial strain selected from the group consisting of *Lactobacillus plantarum* HEAL 9, which is deposited as DSM 15312, *Lactobacillus plantarum* HEAL 19, which is deposited as DSM 15313, and *Lactobacillus plantarum* HEAL 99, which is deposited as DSM 15316.

23. A food comprising:
(a) at least one isolated probiotic bacterial strain selected from the group consisting of *Lactobacillus crispatus* VPC5, which is deposited as DSM 16735, *Lactobacillus crispatus* VPC40, which is deposited as DSM 16736, *Lactobacillus crispatus* VPC70, which is deposited as DSM 16738, *Lactobacillus crispatus* VPC71, which is deposited as DSM 16739, *Lactobacillus crispatus* VPC77, which is deposited as DSM 16740, *Lactobacillus crispatus* VPC111, which is deposited as DSM 16741, *Lactobacillus crispatus* VPC130, which is deposited as DSM 16742, *Lactobacillus crispatus* VPC177, which is deposited as DSM 16743, *Lactobacillus gasseri* VPG44, which is deposited as DSM 16737; and
(b) optionally, at least one isolated probiotic bacterial strain selected from the group consisting of *Lactobacillus plantarum* HEAL 9, which is deposited as DSM 15312, *Lactobacillus plantarum* HEAL 19, which is deposited as DSM 15313, and *Lactobacillus plantarum* HEAL 99, which is deposited as DSM 15316.

24. A food supplement comprising:
(a) at least one isolated probiotic bacterial strain selected from the group consisting of *Lactobacillus crispatus* VPC5, which is deposited as DSM 16735, *Lactobacillus crispatus* VPC40, which is deposited as DSM 16736, *Lactobacillus crispatus* VPC70, which is deposited as DSM 16738, *Lactobacillus crispatus* VPC71, which is deposited as DSM 16739, *Lactobacillus crispatus* VPC77, which is deposited as DSM 16740, *Lactobacillus crispatus* VPC111, which is deposited as DSM 16741, *Lactobacillus crispatus* VPC130, which is deposited as DSM 16742, *Lactobacillus crispatus* VPC177, which is deposited as DSM 16743, *Lactobacillus gasseri* VPG44, which is deposited as DSM 16737; and
(b) optionally, at least one isolated probiotic bacterial strain selected from the group consisting of *Lactobacillus plantarum* HEAL 9, which is deposited as DSM 15312, *Lactobacillus plantarum* HEAL 19, which is deposited as DSM 15313, and *Lactobacillus plantarum* HEAL 99, which is deposited as DSM 15316.

25. The composition according to claim 7, wherein said food product is selected from the group consisting of bread, cheese, yogurt, juice, health bars, spreads, biscuits and cereals.

26. The composition according to claim 4, wherein said at least one probiotic bacterial strain is present in an amount giving, when consumed, an effective daily dose of $10^9$ to $10^{10}$ CFU.

27. The composition according to claim 11, wherein said composition is administered orally, and wherein said at least one probiotic bacterial strain is present in an amount giving an effective daily dose of from $10^9$ to $10^{10}$ CFU.

* * * * *